US00PP20243P2

(12) United States Plant Patent
Robb

(10) Patent No.: US PP20,243 P2
(45) Date of Patent: Sep. 1, 2009

(54) ***RHAPHIOLEPIS* PLANT NAMED 'PARHAP'**

(50) Latin Name: *Rhaphiolepis×indica*
Varietal Denomination: Parhap

(75) Inventor: John Robb, Kulnurra (AU)

(73) Assignee: The Paradise Seed Company Pty. Ltd., Kulnurra (AU)

( * ) Notice: Subject to any disclaimer, the term of this patent is extended or adjusted under 35 U.S.C. 154(b) by 0 days.

(21) Appl. No.: 12/070,247

(22) Filed: Feb. 15, 2008

(51) Int. Cl.
*A01H 5/00* (2006.01)

(52) U.S. Cl. ..... Plt./254
(58) Field of Classification Search ..... Plt./254
See application file for complete search history.

*Primary Examiner*—Susan B McCormick Ewoldt
(74) *Attorney, Agent, or Firm*—Mark P. Bourgeois

(57) ABSTRACT

A new and distinct cultivar of *Rhaphiolepis* plant named 'Parhap' characterized by a compact growth habit, resistance to leaf spot disease, white uniform flowers and cold hardiness.

1 Drawing Sheet

Botanical classification: *Rhaphiolepis×indicia.*
Variety denomination: 'Parhap'.

BACKGROUND OF THE INVENTION

The present Invention relates to a new and distinct cultivar of *Rhaphiolepis* plant, botanically known as *Rhaphiolepis×inidica* and hereinafter referred to by the name 'Parhap'. *Rhaphiolepis* species are grown chiefly as ornamental flowering and evergreen shrubs for low hedges, groupings, and mass plantings.

The new cultivar originated from seed collected from the seed or female parent plant *Rhaphiolepis indica* 'Fergusonii' (not patented). The male or pollen parent plant is unknown. The seeds were grown out and 'Parhap' was discovered and selected as a single plant in 1996 in Kulnura in the state of New South Wales, Australia.

The first asexual reproduction of 'Parhap' was in 2001 by terminal cuttings in Kulnura, New South Wales, Australia. The unique features of this new *Rhaphiolepis* have proven stable and reproduced true to type in successive generations of asexual reproduction.

SUMMARY OF THE INVENTION

The following traits have been repeatedly observed and are determined to be the unique characteristics of 'Parhap'. These characteristics in combination distinguish 'Parhap' as a new and distinct cultivar:

1. Compact growth habit.
2. Resistance to leaf spot disease caused by *Entomosporium* spp.
3. White uniform flowers.
4. Cold hardiness.

The closest comparison cultivar is the seed parent plant 'Fergusonii'. *Rhaphiolepis* 'Parhap' is different from 'Fergusonii' in the following characteristics:

| Characteristic | 'Parhap' | 'Fergusonii' |
|---|---|---|
| Leaf: width of blade | Medium | Very narrow to narrow |
| Leaf: shape | oblanceolate | elliptic |
| Leaf: undulation of margin | Very weak | Strong |
| Leaf: curvature of longitudinal axis | Straight | Recurved |
| Leaf: glossiness of upper side | Medium to strong | Medium |
| Leaf: colour | Dark Green | Light to medium green |
| Leaf: disease resistance | Strong | Medium |
| Fruit: degree of fruiting | Absent to very weak | Strong |
| Filament: degree of anthocyanin coloration | Strong | Weak to medium |
| Calyx: degree of anthocyanin coloration | Strong | Weak to medium |

In comparison to the variety 'Snowcap' (U.S. Plant Pat. No. 15,544), 'Parhap' has foliage that remains green in cooler months. The foliage of 'Snowcap' turns a burgundy color during cooler months. 'Snowcap' also produces berries after flowering, while 'Parhap' does not.

BRIEF DESCRIPTION OF THE PHOTOGRAPH

The accompanying sheet of photographs illustrate the distinguishing traits of *Rhaphiolepis* 'Parhap'.

The top photograph is an overall view of a 12 month old plant.

The bottom photograph is an enlarged view of the flowers.

The photographs were taken using conventional techniques and although colors may appear different from actual colors due to light reflectance it is as accurate as possible by conventional photographic techniques.

DETAILED BOTANICAL DESCRIPTION

The new *Rhaphiolepis* has not been observed under all possible environmental conditions. The phenotype may vary somewhat with variations in environment such as temperature and light intensity, without, however, any variance in genotype.

The following is a detailed description of the new *Rhaphiolepis* cultivar named 'Parhap'. Data was collected in Kulnura, New South Wales, Australia from 12 month old plants raised in 20 cm. pots in commercial grade, soil-less potting mix. In the following description, color references are made to The Royal Horticultural Society Colour Chart, 1995 Edition.

Botanical classification: *Rhaphiolepis*×*indica* cultivar 'Parhap'.

Parentage:

Female parent: *Rhaphiolepis indica* 'Fergusonii'.

Male parent: Unknown.

Propagation: Terminal or softwood cuttings.

Root description: Fine and fibrous.

Low temperature tolerance: USDA zone 7.

High temperature tolerance: 40 degrees Centigrade.

Drought tolerance: Moderate.

Plant description:

Habit: Bushy shrub; shape, globose; overall dimensions; 1.1 meters in height and 95 centimeters in width;

Stem: Lateral branch dimensions: 18 cm. in length and 6 cm. in diameter; texture, rough; color, 199B.

Leaf: Dimensions 35 millimeters in length and 26 millimeters in width; attitude, semi-erect; arrangement, alternate; petiole, 9 mm. in length and 2 mm. in diameter; shape, oblanceolate; apex, obtuse; base, attenuate; incision of margin, present, crenate; undulation of margin very weak; shape in cross section, concave; curvature of longitudinal axis, straight; glossiness of upper side, medium to strong; color, upper surface dark green RHS 147A, lower surface RHS 146C;

Inflorescence: Flowering season, spring to summer; type, single; attitude, erect; diameter, 27 millimeters.

Bud: Dimensions, 5 mm. in length and 2.5 mm. in diameter; shape, elliptical; color, 155A.

Flower: Flowers arranged in broad pyramidical panicles; width, 5 to 7.5 cm; fragrance, absent.

Petal: Dimensions, 10 mm. in length and 6 mm. in diameter; shape, obovate; color, upper surface white RHS 155D; lower surface 155D.

Calyx: Dimensions, 5 mm. in length and 2.5 mm. in diameter; color, 196B.

Peduncle: Strength, strong; dimensions, 3.5 cm. in length and 0.6 cm. in diameter, color, 147A.

Reproductive organs:

Stamens, About 8 per flower; anther shape, oval; anther length, 0.7 mm.; anther color, 11D; pollen amount, moderate.

Pistils: Length, 2 mm.; stigma shape, rounded, stigma color, 155D.

Seed production: Has not been observed.

Disease resistance: After growing plants in Kulnura surrounded with plants infected with leaf spot, *Entomosporium* spp., 'Parhap' remained vigorous and disease free while less resistant varieties were affected by leaf spot disease.

Pest resistance: Has not been observed.

What is claimed is:

1. A new and distinct variety of *Rhaphiolepis* plant named 'Parhap' as described and illustrated.

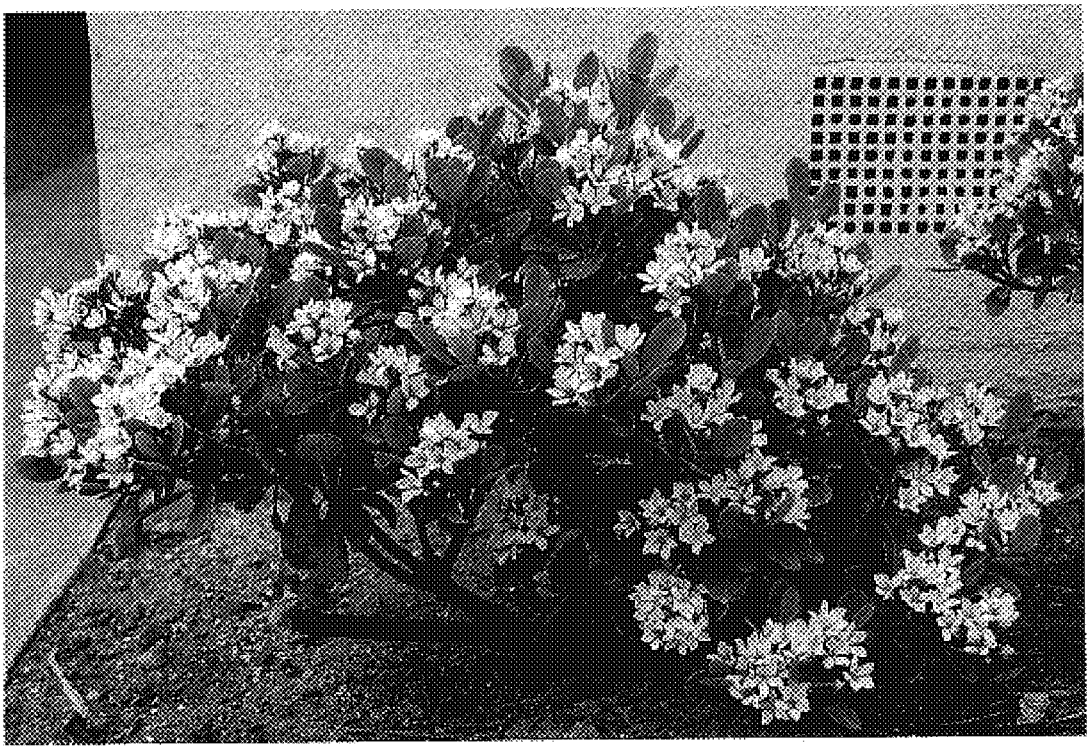
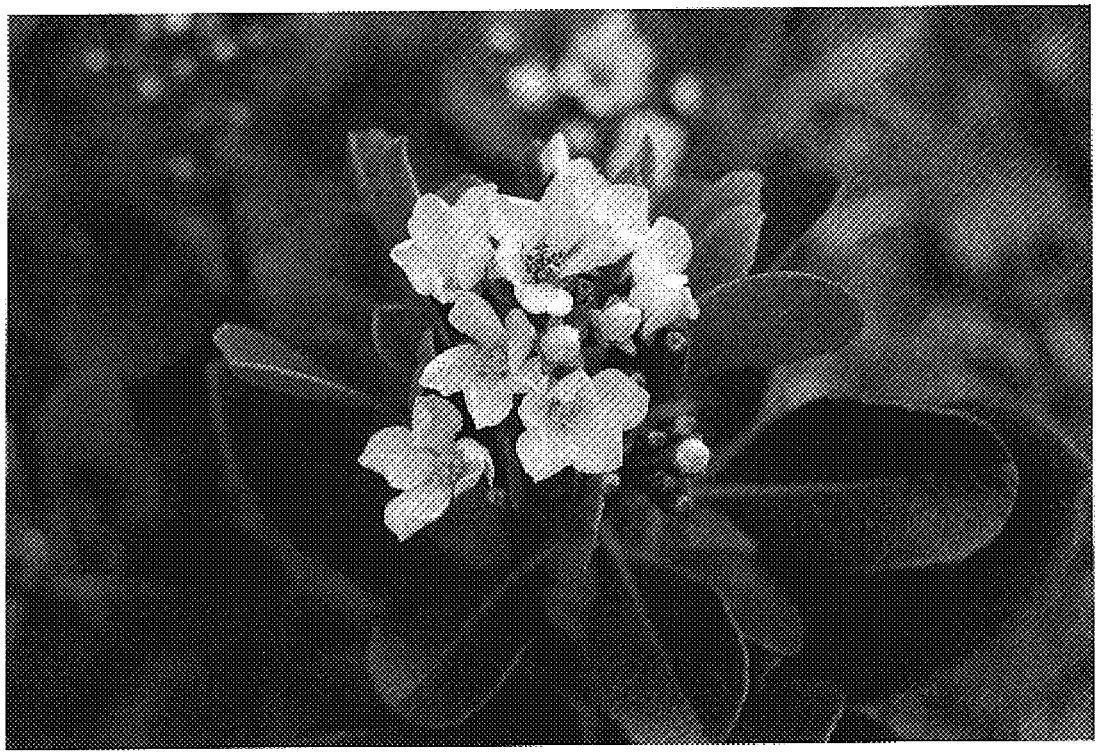

* * * * *